United States Patent
Sramek

(10) Patent No.: US 12,310,893 B2
(45) Date of Patent: May 27, 2025

(54) SYSTEM AND METHOD FOR A PATIENT-INVISIBLE LASER TREATMENT ALIGNMENT PATTERN IN OPHTHALMIC PHOTOMEDICINE

(71) Applicant: IRIDEX Corporation, Mountain View, CA (US)

(72) Inventor: Chris Sramek, Half Moon Bay, CA (US)

(73) Assignee: IRIDEX Corporation, Mountain View, CA (US)

(*) Notice: Subject to any disclaimer, the term of this patent is extended or adjusted under 35 U.S.C. 154(b) by 961 days.

(21) Appl. No.: 17/398,323

(22) Filed: Aug. 10, 2021

(65) Prior Publication Data
US 2022/0062036 A1 Mar. 3, 2022

Related U.S. Application Data

(63) Continuation of application No. 15/874,984, filed on Jan. 19, 2018, now Pat. No. 11,116,663.

(51) Int. Cl.
*A61F 9/008* (2006.01)
*A61B 3/00* (2006.01)
(Continued)

(52) U.S. Cl.
CPC ............ *A61F 9/008* (2013.01); *A61B 3/0008* (2013.01); *A61B 3/0025* (2013.01); *A61B 3/13* (2013.01); *A61B 3/135* (2013.01); *A61F 9/00821* (2013.01); *A61N 5/0613* (2013.01); *G02B 21/0012* (2013.01); *A61B 2018/2025* (2013.01);
(Continued)

(58) Field of Classification Search
CPC .................. A61F 9/008; A61F 9/00821; A61F 2009/00863; A61B 3/0008; A61B 3/0025; A61B 3/13; A61B 3/135; A61B 18/22; A61B 2018/2025; A61B 2090/306;
(Continued)

(56) References Cited

U.S. PATENT DOCUMENTS

| 4,196,980 A | 4/1980 | Heine |
| 4,801,198 A | 1/1989 | Heacock et al. |

(Continued)

FOREIGN PATENT DOCUMENTS

| CN | 202044247 | 11/2011 |
| CN | 102768403 | 11/2012 |

(Continued)

OTHER PUBLICATIONS

European Communication Pursuant to 94(3) EPC for Application No. EP14847231.9, mailed Feb. 18, 2021, 6 pages.
(Continued)

*Primary Examiner* — Mohammed A Hasan
(74) *Attorney, Agent, or Firm* — Kilpatrick Townsend & Stockton LLP

(57) ABSTRACT

An ophthalmic illumination method and system with a head-up display imaging system is provided wherein a therapeutic light is generated by a first laser light source configured to generate therapeutic light and a near-infrared wavelength of an alignment pattern is generated by a second laser light source, where the therapeutic light is directed upon an eye to be examined or treated in accordance with the alignment pattern.

20 Claims, 5 Drawing Sheets

(51) Int. Cl.
- *A61B 3/13* (2006.01)
- *A61B 3/135* (2006.01)
- *A61N 5/06* (2006.01)
- *G02B 21/00* (2006.01)
- *A61B 18/20* (2006.01)
- *A61B 18/22* (2006.01)
- *A61B 90/30* (2016.01)
- *A61N 5/067* (2006.01)

(52) U.S. Cl.
CPC ......... *A61B 18/22* (2013.01); *A61B 2090/306* (2016.02); *A61F 2009/00863* (2013.01); *A61N 2005/063* (2013.01); *A61N 5/067* (2021.08)

(58) Field of Classification Search
CPC ................. A61N 5/0613; A61N 5/067; A61N 2005/063; G02B 21/0012
USPC ...................................................... 351/221
See application file for complete search history.

(56) References Cited

U.S. PATENT DOCUMENTS

| | | | |
|---|---|---|---|
| 4,917,486 | A | 4/1990 | Raven et al. |
| 4,995,716 | A | 2/1991 | Warnicki et al. |
| 5,912,720 | A | 6/1999 | Berger et al. |
| 5,943,118 | A | 8/1999 | Koschmieder et al. |
| 6,299,310 | B1 | 10/2001 | Reis |
| 6,394,601 | B1 | 5/2002 | Bettinger |
| 7,766,481 | B2 | 8/2010 | Dick et al. |
| 2002/0051116 | A1 | 5/2002 | Van Saarloos et al. |
| 2003/0071970 | A1 | 4/2003 | Donnerhacke et al. |
| 2004/0061932 | A1 | 4/2004 | Pensel et al. |
| 2004/0165146 | A1* | 8/2004 | Della Vecchia ......... A61B 3/14 351/221 |
| 2005/0107708 | A1 | 5/2005 | Wrobel et al. |
| 2005/0277913 | A1 | 12/2005 | McCary |
| 2005/0288564 | A1 | 12/2005 | Iuliano |
| 2007/0126985 | A1 | 6/2007 | Wiltberger et al. |
| 2008/0015553 | A1 | 1/2008 | Zacharias |
| 2008/0018987 | A1 | 1/2008 | Miller |
| 2009/0093798 | A1 | 4/2009 | Charles |
| 2009/0153796 | A1 | 6/2009 | Rabner |
| 2010/0202036 | A1 | 8/2010 | Minor et al. |
| 2010/0271594 | A1 | 10/2010 | Bergner et al. |
| 2011/0052042 | A1 | 3/2011 | Ben Tzvi |
| 2012/0026462 | A1* | 2/2012 | Uhlhorn ............. G01B 9/02028 351/246 |
| 2012/0165905 | A1 | 6/2012 | Liesfeld et al. |
| 2012/0165906 | A1 | 6/2012 | Liesfeld et al. |
| 2013/0128228 | A1 | 5/2013 | Zhou et al. |
| 2013/0194548 | A1 | 8/2013 | Francis et al. |
| 2013/0301003 | A1 | 11/2013 | Wells et al. |
| 2014/0361957 | A1 | 12/2014 | Hua et al. |
| 2016/0256324 | A1 | 9/2016 | Suzuki |
| 2016/0287441 | A1 | 10/2016 | Palanker et al. |
| 2018/0092528 | A1* | 4/2018 | Takeno .................. A61B 3/102 |
| 2019/0224043 | A1* | 7/2019 | Sramek .................. A61F 9/008 |

FOREIGN PATENT DOCUMENTS

| | | |
|---|---|---|
| DE | 1015314 | 9/1957 |
| EP | 0188470 | 7/1986 |
| EP | 0221649 | 7/1987 |
| EP | 1400829 | 3/2004 |
| EP | 2012696 | 1/2009 |
| JP | 61502800 | 12/1986 |
| JP | 62109542 | 5/1987 |
| JP | 01500009 | 1/1989 |
| JP | 08117193 | 5/1996 |
| JP | 2000262476 | 9/2000 |
| JP | 2002071312 A | 3/2002 |
| JP | 2016505312 A | 2/2016 |
| JP | 2016111475 A | 6/2016 |
| JP | 2016112358 A | 6/2016 |
| WO | 8600512 | 1/1986 |
| WO | 8705204 | 9/1987 |
| WO | 0027273 | 5/2000 |
| WO | 2009145738 | 12/2009 |
| WO | 2012060724 | 5/2012 |

OTHER PUBLICATIONS

Extended European Search Report for Application No. EP14847231.9, mailed May 15, 2017, 8 pages.
International Search Report and Written Opinion for Application No. PCT/US2014/057360, Mailed Dec. 24, 2014, 8 pages.
International Search Report and Written Opinion for Application No. PCT/US2014/068301, Mailed On Feb. 20, 2015, 15 pages.
International Search Report and Written Opinion for Application No. PCT/US2019/013421, Mailed Apr. 4, 2019, 11 pages.
Notification of Reasons for Refusal for Application No. JP2016-538042, mailed Aug. 14, 2018, 8 pages.
Palanker et al., "The Impact of Pulse Duration and Burn Grade on Size of Retinal Photocoagulation Lesion: Implications for Pattern Density", Retina, The Journal of Retinal and Vitreous Diseases, vol. 31, No. 8, 2011, pp. 1664-1669.

* cited by examiner

SYSTEM AND METHOD FOR A PATIENT-INVISIBLE LASER TREATMENT ALIGNMENT PATTERN IN OPHTHALMIC PHOTOMEDICINE

CROSS-REFERENCE TO RELATED APPLICATIONS

The present application is a Continuation of U.S. patent application Ser. No. 15/874,984 filed Jan. 19, 2018, the disclosure of which is incorporated herein by reference for all purposes.

FIELD OF THE INVENTION

The present invention is generally directed to ophthalmic photomedicine, and more specifically to systems and methods for generating laser treatment alignment patterns on a patient's eye.

BACKGROUND OF THE INVENTION

Ophthalmic photomedicine (e.g., laser treatment or laser surgery) employing multiple-spot laser therapy is widely used today to treat various conditions of the eye such as diabetic retinopathy and age-related macular degeneration. Typically, multiple-spot laser therapy is performed by utilizing a slit-lamp-mounted laser treatment device or probes that are inserted into the patient's eye. In a slit-lamp-mounted laser treatment device, a slit lamp is arranged to allow illumination and microscopic viewing of a patient's eye. Slit lamps used in laser treatment or laser surgery typically include a high-brightness illuminator, which can be focused to shine a desired light pattern into a patient's eye, and a microscope mounted on a shared pivot point. The shared pivot point allows the viewing angle of the illuminator and microscope to be changed as often as desired without moving the field of illumination or visualization.

Laser treatment or laser surgery also requires the high-precision aiming of a treatment laser beam. A visible wavelength (e.g., 400-700 nm) aiming beam is often used to generate an alignment pattern (e.g., one or more spots, or a scanned image) that marks a target area on or within a patient's eye for guiding the treatment beam. The separate aiming beam and treatment beam are typically combined to propagate in a shared path, and both beams are projected onto the target area on or within the patient's eye. For example, a physician who is viewing the patient's eye can adjust the alignment pattern such that it overlays the desired target area. The physician may then activate the treatment beam, which is coincident with the alignment pattern. In this configuration, the alignment pattern is a so-called "real" image because the image is an actual pattern of light projected onto, and subsequently viewed from, the actual target area.

While the use of a visible wavelength aiming beam that is coincident with the treatment beam at the targeted eye structure works well in most situations, this technique does have certain shortcomings. For example, because the aiming beam is optically coupled to the patient's eye, the patient sees the alignment pattern before and/or during treatment, which can increase patient anxiety during the procedure. There may also be associated safety and/or discomfort issues because the aiming beam irradiance is generally higher in the patient's eye than in the physician's eye. Further, in some procedures it is preferable for the patient to not see the aiming beam at all. For example, in treatment near the eye's macula (i.e., the central region of highest visual acuity) the patient may inadvertently fix their gaze on the aiming beam resulting in unintended destruction of the patient's central vision.

Therefore, a need exists for an improved technique for generating alignment patterns in ophthalmic procedures.

BRIEF SUMMARY OF THE INVENTION

An ophthalmic photomedicine method and apparatus is provided that allows for the generation of an alignment pattern (i.e., treatment pattern) during procedures such as laser surgery or laser treatment where the alignment pattern is visible only to the individual (e.g., physician) administering the surgery or treatment but not the intended patient thereof.

In accordance with an embodiment, a first optical element is configured to direct light from a light source upon an organic object, illustratively, the eye of an individual (i.e., patient) to be examined and treated. A micro-display projector forms a second optical element and is configured to generate a micro-display image including information associated with the eye to be examined. The micro-display projector may include one of a liquid crystal on silicon (LCoS), digital-micro-mirror (DMD) or micro-electro-mechanical systems (MEMS) micro-scanner, and one of a light-emitting diode (LED) or red-green-blue (RGB) laser light source. A third optical element is configured to (i) receive reflected light from the eye resulting from the light directed upon the eye; (ii) receive the micro-display image; and (iii) transmit at least a portion of the reflected light and at least a portion of the micro-display image.

Advantageously, in accordance with an embodiment, the system provides for a "real" alignment pattern where the aiming light is actually projected onto the target tissue (e.g., the patient's retina) and real-time image sensing is facilitated. In an embodiment, an alignment laser source generates a near-infra-red (NIR) alignment wavelength (i.e., an NIR aiming laser) for forming an alignment pattern for projection on a target tissue of the eye. As such, this eliminates the need for any superimposed target patterns on the patient's eye given the projection of the aiming light onto the target tissue.

In accordance with an embodiment, the third optical element may be further configured to transmit a stereoscopic image of the portion of the reflected light and the portion of the micro-display image. The third optical element may be a beam-splitter.

These and other advantages of the invention will be apparent to those of ordinary skill in the art by reference to the following detailed description and the accompanying drawings.

DETAILED DESCRIPTION OF THE INVENTION

Figure 1:
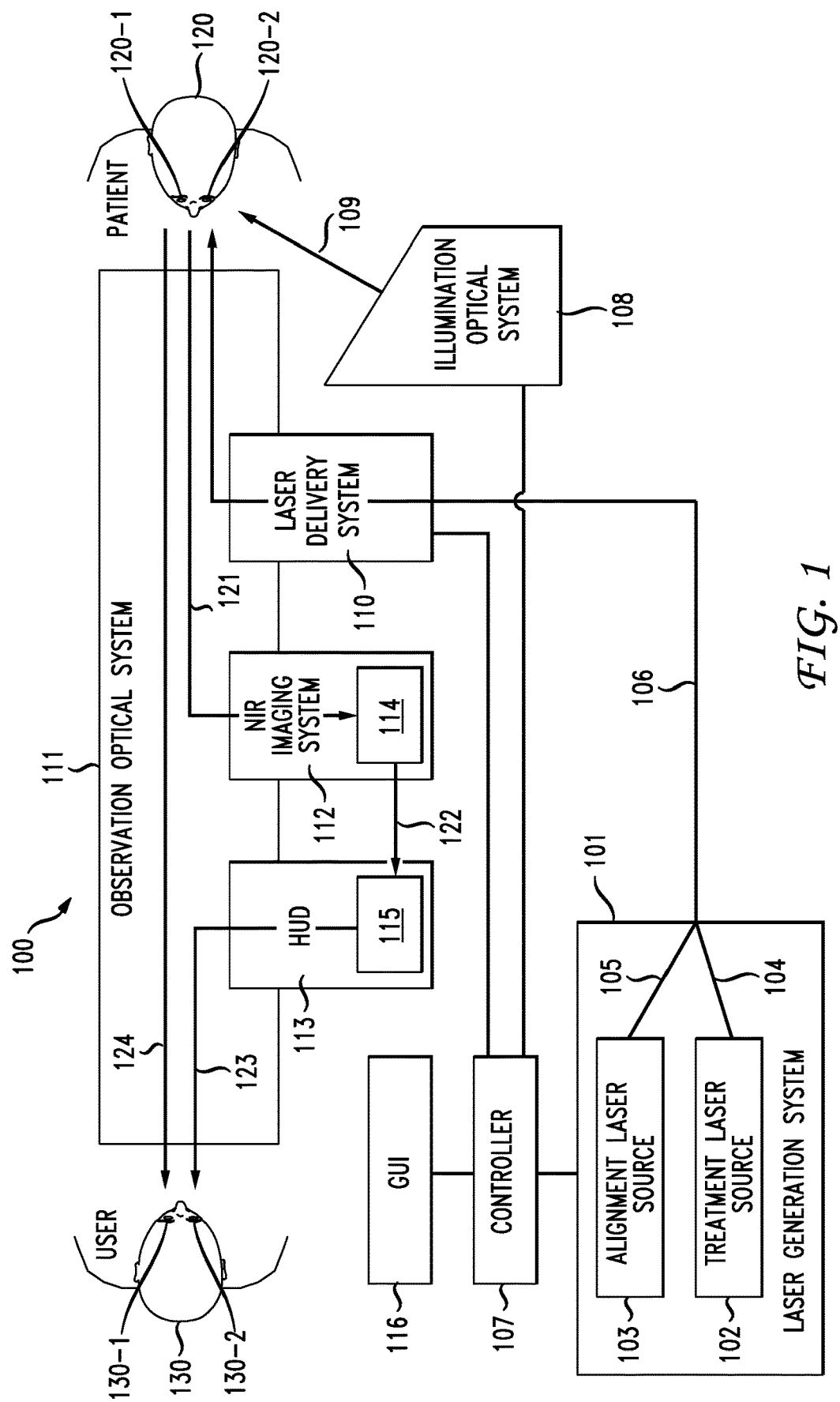
FIG. 1 shows an ophthalmic illumination and microscopic viewing system in accordance with an embodiment.

FIG. 1 shows an ophthalmic illumination and microscopic viewing system 100 in accordance with an embodiment. Ophthalmic illumination and microscopic viewing system 100 comprises a laser generation system 101, laser delivery system 110, observation optical system 111, illumination optical system 108, Near-Infra-Red (NIR) imaging system 112, and a Heads-up (or Head-up) display (HUD) system 113.

Laser generation system 101 includes a treatment laser source 102 and an alignment laser source 103 and may be illustratively operated by user 130 (e.g., a treating physician or other practitioner) who is examining patient 120. Laser generation system 101 is communicably coupled with a controller 107 which is communicably coupled with a graphical user interface 116. Treatment laser source 102 generates therapeutic light (i.e., "treatment laser") 104 to be used for treatment of an organic object, illustratively, patient's eye 120-1 or patient's eye 120-2. Alignment laser source 103 generates a near-infra-red (NIR) alignment wavelength (i.e., "NIR aiming laser") 105 for projection on a target tissue of the patient's eye 120-1 in a form of an alignment pattern. Laser generation system 101 is configured to couple treatment laser 104 generated by treatment laser source 102 with NIR aiming laser 105 generated by alignment laser source 103 into one or more optical fibers 106 to propagate coupled treatment laser 104 and NIR aiming laser 105 to laser delivery system 110. It will be understood that any reference herein to patient's eye 120-1 will apply equally to patient's eye 120-2 and for ease of explanation herein below, reference to patient's eye 120-1 will be utilized. Similarly, it will be understood that any reference herein to user's eye 130-1 will apply equally to patient's eye 130-2 and for ease of explanation herein below, reference to user's eye 130-1 will be utilized.

Laser delivery system 110 is a component of an observation optical system 111 configured to propagate coupled treatment laser 104 and NIR aiming laser 105 through the observation optical system 111 to patient's eye 120-1. Observation optical system 111 is configured to provide a direct magnified view of patient's eye 1201 to user's eye 130-1 and/or user's eye 130-2. Illumination optical system 108 is configured to illuminate the patient's eye 120-1 with visible light 124 and near infrared light 109.

In the embodiment, NIR imaging system 112 includes a charge-coupled device (CCD) 114. The NIR imaging system 112 is positioned to capture and direct an NIR wavelength 121 scattered from the eye tissue of the patient's eye 120-1 to CCD 114. In an embodiment, CCD 114 includes a notch filter configured to attenuate wavelengths other than the NIR aiming laser 105. The NIR imaging system 112 may include a beam-splitter configured to perform the operations of directing NIR wavelength 121 scattered from the eye tissue of patient's eye 120-1 to CCD 114. An exemplary beam-splitter may include a glass or plastic cube, a half-silvered mirror (e.g., a sheet of glass or plastic with a thin coating of metal or dichroic optical coating) or a dichroic mirrored prism. In the embodiment, instead of a notch filter, CCD 114 may include a long-pass NIR filter to overlay NIR image of patient's eye 120-1 with a direct view.

HUD system 113 is configured to receive the NIR image of the patient's eye 120-1, superimpose the NIR image of the patient's eye 120-1 with direct image of patient's eye 120-1 and propagate the superimposed image of patient's eye 120-1 to user eye 130-1. In an embodiment, the HUD display system 113 includes a light source, microdisplay, collimating optics, beam splitting optics for providing images to the observation paths (e.g., left and right paths), and beam-splitters in the observation path for directing visible light toward user 130.

In the embodiment, optical fiber 108, in which the treatment laser 104 and NIR aiming laser 105 are co-aligned and coupled, is routed through laser delivery system 110 to observation optical system 111 (e.g., ophthalmoscope). Further, controller 107 is configured to generate and transmit user commands to laser generation system 101 based on user input received via GUI 116. Controller 107 may also be configured to receive inputs from one or more external sources (e.g. a camera flash trigger or a computer processing real-time slit-lamp video). It is to be understood that GUI 116 may be a touch-screen display, LCD with a mouse/trackpad interface, and the like.

In the embodiment, ophthalmic illumination and microscopic viewing system 100 is configured to employ the same fiber(s) for treatment laser 104 and NIR aiming laser 105. In an alternative embodiment, ophthalmic illumination and microscopic viewing system 100 may be configured to employ separate (i.e., different) fibers dedicated for treatment laser 104 and NIR aiming laser 105 within laser delivery system 110.

In accordance with an embodiment, the observation optical system 111 is configured to propagate a composite image of the patient's eye 120-1 with an overlaid image of an alignment pattern where five to fifteen percent (5-15%) of light is associated with the overlaid image, resulting in a high-quality overlaid image of the patient's eye 120-1. For example, about ninety percent (90%) of the overlaid image passes through the beam splitter. The overlaid image is practically invisible when only about ten percent (10%) of the overlaid image is transmitted. One skilled in the art will appreciate that other ratios of projected light allowed to be passed through are possible. Further, in an embodiment, the observation optical system 111 is configured to preferably allow between about ninety to ninety-nine (90-99%) of the reflected light 124 to pass through from patient's eye 120-1 toward user 130 (and user's eye 130-1). For example, about one percent (1%) of the reflected light 124 is lost when the observation optical system 111 is configured to allow ninety-nine (99%) of the reflected light 124 from patient's eye 120-1 to pass through toward user 130 (and user's eye 130-1). Again, one skilled in the art will appreciate that other ratios of reflected light 124 allowed to pass through or be reflected are possible.

When the ophthalmic illumination and microscopic viewing system 100 is using a "real" alignment pattern, the NIR aiming laser 105 is actually projected onto the target tissue. Actual projection of NIR aiming laser 105 onto the target tissue of patient's eye 120-1 has a distinct advantage over the "virtual" approach described above in that the observed (via HUD system 113) aiming beam defocuses realistically, since what is being imaged on retina of the patient's eye 120-1 is an actual defocused NIR aiming laser 105 rather than a virtual projection. That is, user 130 directly observes (illustratively, user's eye 130-1) patient's eye 120-1 through the observation optical system 111, and a view of the retina of patient's eye 120-1 in NIR light (showing only the aiming laser 105) is superimposed on the direct view with the HUD system 113.

A light scattered from target tissue of the patient's eye 120-1 is collected within the observation optical system 111. Visible light 124 is directly viewed by user eye 130-1 through an eyepiece of the observation optical system 111.

The NIR aiming laser 105 is reflected as reflection wavelength 121 into the NIR imaging system 112. The NIR imaging system 112, using, for example, a notch filter, attenuates all wavelengths outside the narrow band corresponding to the wavelength of NIR aiming laser 105. Upon receiving reflection wavelength 121 of NIR aiming laser 105, the NIR imaging system 112 generates video image frames of NIR beam on eye tissue of the patient's eye 120-1 and transmits the generated video image frames to the HUD display system 113.

It is to be understood that a composite image of patient's eye 120-1 with an overlaid image of the alignment pattern may also include concurrent information, including any type of image or data that may be associated with patient's eye 120-1. For example, concurrent information may include patient information, the current time and date, or other information that may be of use in a clinical environment. In another example, concurrent information may include measurement information, such as a measurement axis, distance, area, scale or grid. Measurement information also may include a current illumination area diameter, current slit width, inter-slit spacing, current filter choice, micrometer scale labeling, or circle/ellipse radii, ratios and areas.

When illumination system 108 is used in conjunction with therapy systems including laser systems and other equipment, concurrent information may include one of a treatment parameter or a preoperative image, treatment plan, an aiming beam pattern indicator or a treatment beam target indicator. In yet other example, concurrent information may include information regarding treatment laser parameters, such as, e.g., power, spot-size and spacing.

In an alternative implementation of ophthalmic illumination and microscopic viewing system 100, alignment laser source 103 generating NIR aiming laser 105 may be located within laser delivery system 110. In this case, laser delivery system 110 is configured to use beam-shaping/collimation optics to couple treatment laser 104 with NIR aiming laser 105 into one or more optical fibers within laser delivery system 110. The one or more optical fibers direct coupled treatment laser 104 and NIR aiming laser 105 to patient's eye 120-1.

It is to be understood that laser generation system 101, NIR imaging system 112 and HUD system 113 can be implemented in such a way that there is no data connection between controller 107, NIR imaging system 112 and HUD system 113. In this case, NIR imaging system 112 and HUD system 113 detect NIR light in a narrow band corresponding to the NIR aiming laser 105 and superimposing NIR aiming laser 105 on the direct view of patient's eye 120-1, without data exchange with the controller 107. It is also to be understood that the color of the aiming beam projected by HUD system 113 to the user 130 can be arbitrarily set, as opposed to using an often-used long red wavelengths, to provide maximum user visibility of an alignment beam.

In an alternative embodiment of ophthalmic illumination and microscopic viewing system 100, NIR aiming laser 105 may be generated by treatment laser source 103 using, illustratively, a residual pump prior to frequency doubling. In a further embodiment of ophthalmic illumination and microscopic viewing system 100, NIR aiming laser 105 is configured to have a shared function with a NIR imaging system 112 (e.g., an optical coherence tomography (OCT) or scanning laser opthalmoscope (SLO) imaging system). In a further embodiment, ophthalmic illumination and microscopic viewing system 100 may be configured to include separate NIR channel (e.g., free space or fiber-coupled) with polarizer, cross-polarized before CCD 114 to reduce reflections. In an alternative embodiment, NIR imaging system 112 and HUD system 113 may be configured to share a common beam-splitter having an internal beam-splitter coating to reflect the NIR signal and transmit the visible signal at a 90:10 split-ratio.

Figure 2:
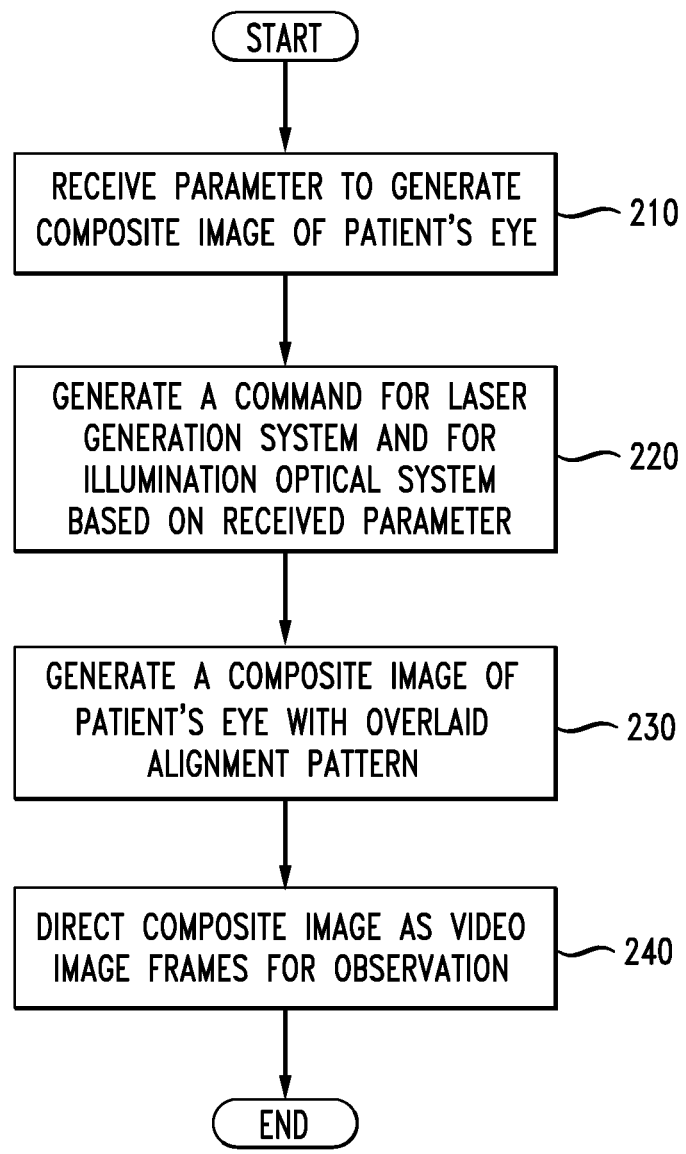
FIG. 2 shows a flowchart of an ophthalmic illumination method in accordance with an embodiment.

FIG. 2 is a flowchart of illustrative operations for an ophthalmic illumination method in accordance with an embodiment. For ease of illustration, FIG. 2 is discussed below with reference also to FIG. 1. At step 210, a parameter for generating a composite image of patient's eye 120-1 is received. Referring to FIG. 1, controller 107 may be illustratively configured to receive, via GUI 116, a parameter for generating the composite image of patient's eye 120-1, wherein the parameter is related to concurrent information relating to patient data, a treatment parameter, a preoperative image, or a treatment plan. Receipt of the parameter by processor 107 initiates an alignment phase of laser treatment. During the alignment phase, visible or invisible (NIR) aiming laser 105 is selected. In an embodiment, the selection of visible or invisible (NIR) aiming laser 105 is implemented as a so-called "aiming visibility" slider bar in GUI where the higher visibility indicator corresponds to visible wavelength and where the lower visibility indicator corresponds to NIR wavelength.

At step 220, a command based on the received parameter is generated for the laser generation system 101 and for the illumination optical system 108. Referring back to FIG. 1, the controller 107 illustratively transmits a command to the illumination optical system 108 to generate a light beam 109 to be directed toward the patient's eye 120-1. Light beam 109 strikes patient's eye 120-1 and is reflected, generating reflected light 124. Reflected light 124 is propagated through the observation optical system 111 toward the user 130, allowing the user to view structures within patient's eye 120-1.

Concurrently, the controller 107 transmits a command to laser generation system 101 for the aiming laser source 103 to generate an aiming laser 105 based on the parameter. The generated NIR aiming laser 105 is directed to patient's eye 120-1 via laser delivery system 110 and projected onto patient's eye 120-1 in the form of an alignment pattern in accordance with the command. Laser delivery system 110 scans at least the X/Y pattern and modifies beam magnification to create a spot size/pattern on eye tissue of patient's eye 120-1 (co-aligned with illumination optical system 118) according to user input to controller 107 via GUI 116.

At step 230, a composite image of patient's eye 120-1 with an overlaid image of the alignment pattern using reflection wavelength 121 of NIR aiming laser 105 is generated in the HUD system 113. To generate a composite image of patient's eye 120-1, the ophthalmic illumination and microscopic viewing system 100 is configured to use virtual spot-size selection for an alignment pattern or real alignment pattern for the NIR aiming laser 105. At step 240, the composite image 123 of patient's eye 120-1 is directed as video image frames for observation to the user 130 through the eyepiece of the observation optical system 111. Accordingly, user 130 receives a composite image that includes an image of patient's eye 120-1 and the overlaid image of the alignment pattern propagated by the reflection wavelength 121 of NIR aiming laser 105. In an embodiment, the composite image of patient's eye 120-1 includes concurrent information relating to patient data, a treatment parameter, a preoperative image, or a treatment plan.

In an embodiment, the observation optical system 111 is configured to transmit approximately ten percent (10%) of reflected light 124 and allow approximately ninety percent (90%) of the reflected light to pass through (i.e., to be lost). The observation optical system 111 also may be configured to allow approximately ninety-nine (99%) of reflected light 124 to pass through toward user 130 and allow approximately one percent (1%) of the reflected light 124 to be reflected and lost. As such, ophthalmic illumination and microscopic viewing system 100 with a micro-display overlaid image source as disclosed herein may serve as a replacement for a slit-lamp illuminator with a traditional overlaid image source.

In the case of virtual spot-size selection, single, the laser delivery system 110 causes minimally sized NIR spot-size to be aimed on retina of the patient's eye 120-1 (using, for example, single mode fiber or directly imaged laser diode emitter). Reflected NIR aiming laser is captured by CCD 114 which calculates a treatment spot-size parameter which is the point-spread function of laser delivery system 110 and observation optical system 112. A calculated treatment spot-size parameter is then communicated from CCD 114 to HUD system 113 via communication link 122. HUD system 113 then performs (illustratively by processor 115) numerical two-dimensional convolution, in a well-known fashion, between CCD video image frames and kernel corresponding to true treatment beam spot-size and HUD system 113 displays the convolved video image frames. The convolved video images are the images of "virtual" correctly-sized and appropriately focused/defocused aiming laser 105.

Figure 3A:
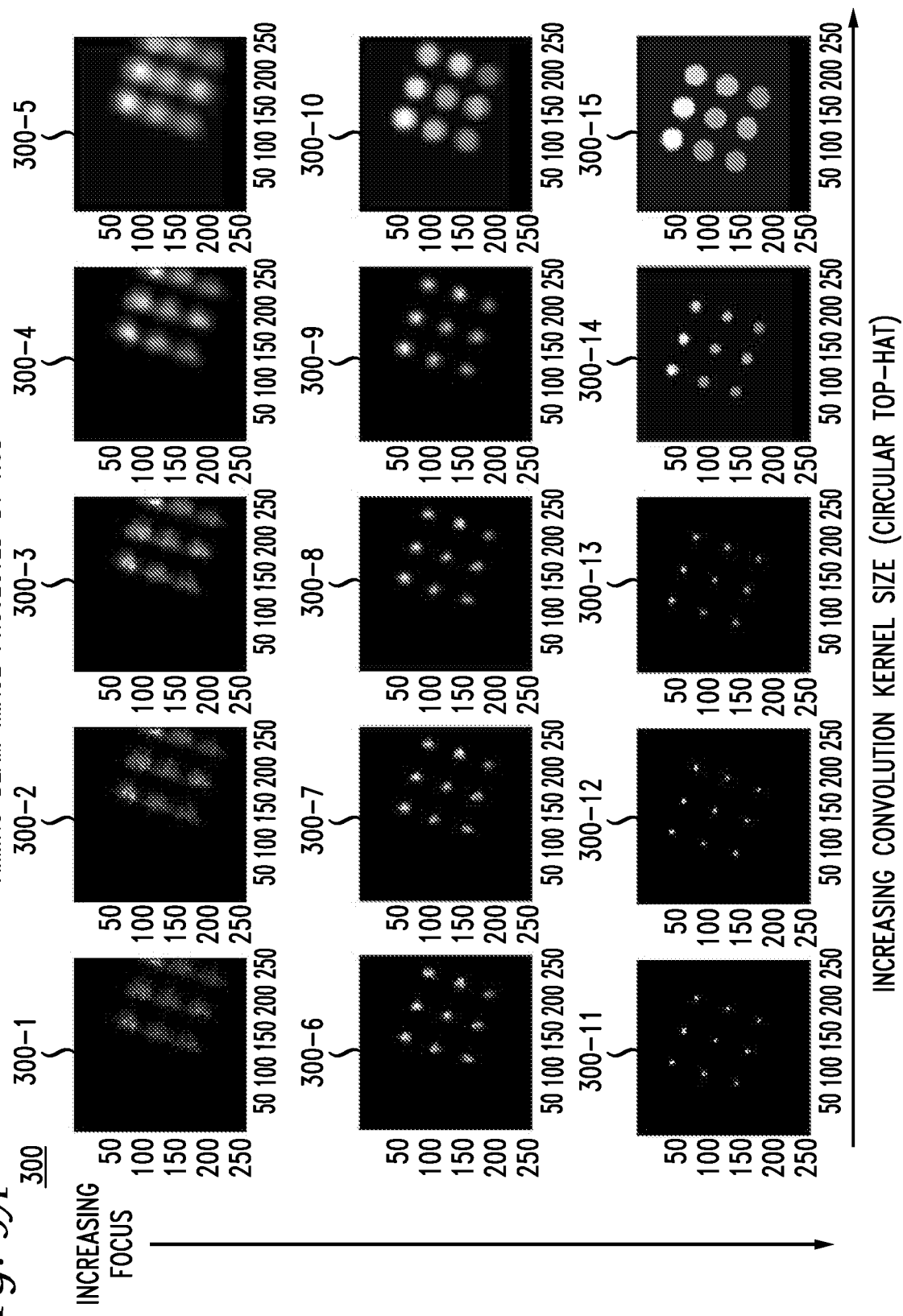
FIGS. 3A and 3B show images of an aiming beam projected by a heads-up display system in accordance with an embodiment.
Figure 3B:
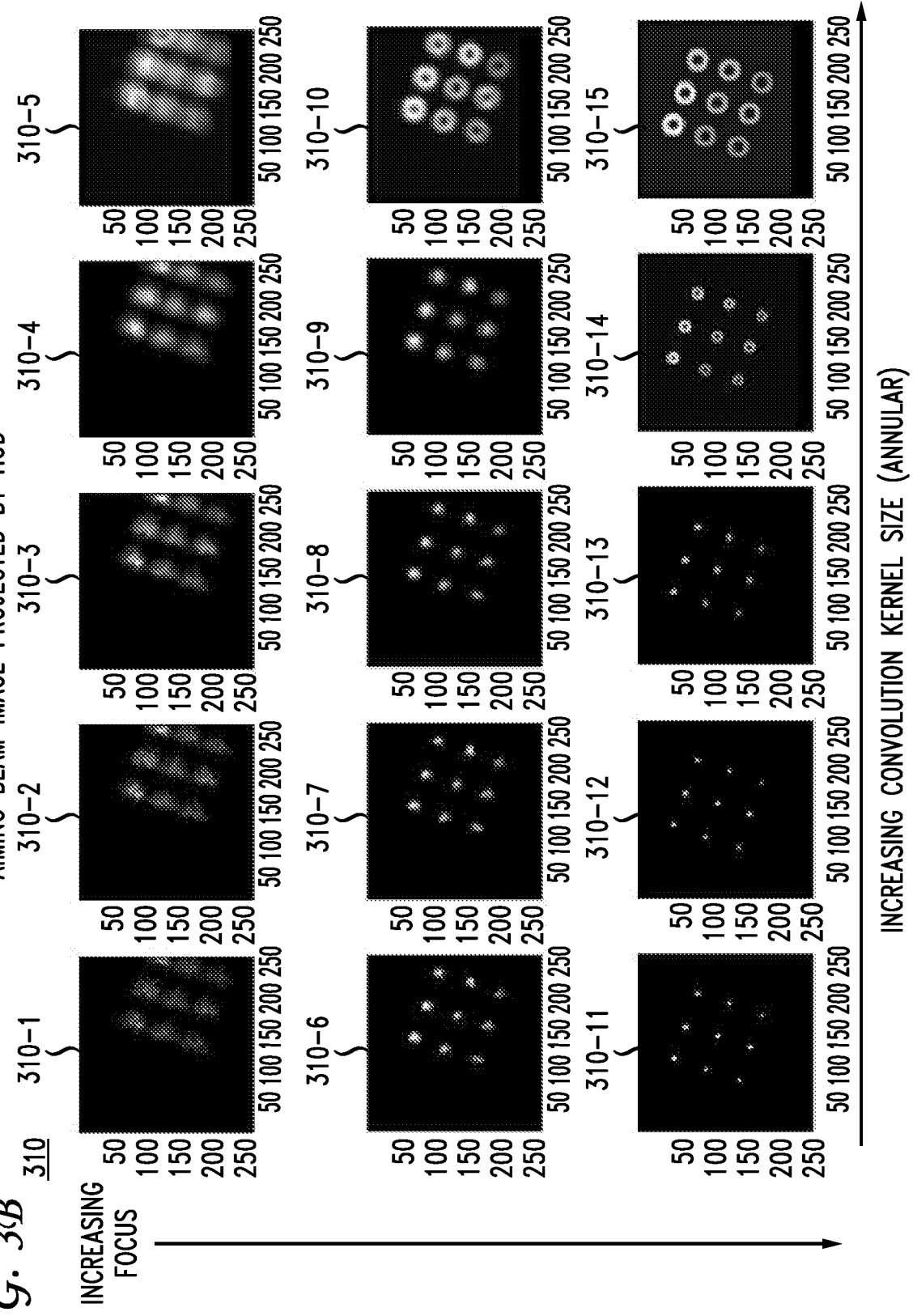

For example, FIGS. 3A and 3B show a series of convolved video image frames. In particular, FIG. 3A shows convolved image 300 (having individual convolved image frames 300-1, 300-2, 300-3, 300-4, 300-5, 300-6, 300-7, 300-8, 300-9, 300-10, 300-11, 300-12, 300-13, 300-14, and 300-15) with the aiming laser 105 having a convolution kernel modified to have a circular top-hat beam shape. Further, FIG. 3B shows convolved image 310 (having individual convolved image frames 310-1, 310-2, 310-3, 310-4, 310-5, 310-6, 310-7, 310-8, 310-9, 310-10, 310-11, 310-12, 310-13, 31014, and 310-15) with the aiming laser 105 having a convolution kernel modified to have an annular beam shape. As shown in FIGS. 3A and 3B, respectively, the delivery of the above-described ophthalmic illumination method and system results in correctly-sized aiming beam with appropriate focusing and defocusing characteristics. In this way, in accordance with the embodiments, an ophthalmic procedure (e.g., laser treatment and/or laser surgery) proceeds such that the responsible health care provider (e.g., physician) has a view of the alignment pattern(s) but not the patient undergoing the procedure. It is to be understood that a convolutional kernel may be modified to change the beam shape of the aiming laser 105 to be of any arbitrary geometric shape. It is also to be understood that convolution kernel can be modified to compensate for imperfections in the true NIR beam shape (e.g. stripe from laser diode source).

Alternatively, ophthalmic illumination and microscopic viewing system 100 may utilize an informationally-enhanced aiming beam based on real-time processing of video image frames. In order to utilize the informationally-enhanced aiming beam, ophthalmic illumination and microscopic viewing system 100 is configured to detect NIR aiming laser 105 as being in or near focus (e.g. convolution with nominal spot pattern or maximum contrast detection), and indicate with, for example, a color change of the HUD-projected aiming beam spot. Alternatively (or concurrently), when it is determined that NIR aiming laser 105 is in focus, ophthalmic illumination and microscopic viewing system 100 is configured to project a circle around the beam to identify a "thermal damage zone" which is pre-computed using a computational model of laser-tissue heating or taken from clinical burn appearance database for different spot-size/pulse duration combinations (as described, e.g., in Daniel Palanker et al. "The Impact of Pulse Duration and Burn Grade on Size of Retinal Photocoagulation Lesion: Implications for Pattern Density" Retina 31.8 (2011): 1664-1669.)

Figure 4:
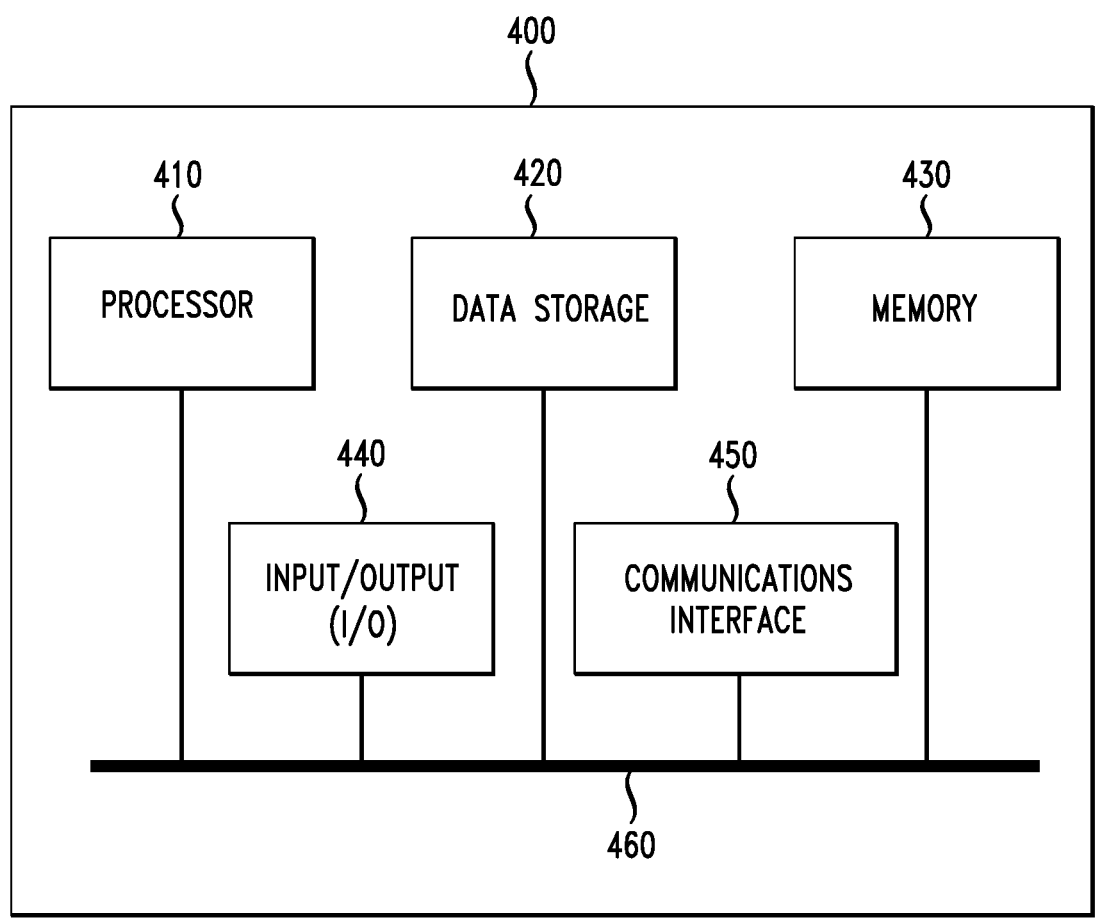
FIG. 4 shows a high-level block diagram of an exemplary computer that may be used for the various embodiments herein.

As detailed above, the various embodiments herein can be embodied in the form of methods and apparatuses for practicing those methods. The disclosed methods may be performed by a combination of hardware, software, firmware, middleware, and computer-readable medium (collectively "computer") installed in and/or communicatively connected to a user device. FIG. 4 is a high-level block diagram of an exemplary computer 400 that may be used for implementing a method for ophthalmic illumination in accordance with the various embodiments herein. Computer 400 comprises a processor 410 operatively coupled to a data storage device 420 and a memory 430. Processor 410 controls the overall operation of computer 400 by executing computer program instructions that define such operations. Communications bus 460 facilitates the coupling and communication between the various components of computer 400.

The computer program instructions may be stored in data storage device 420, or a non-transitory computer readable medium, and loaded into memory 430 when execution of the computer program instructions is desired. Thus, the steps of the disclosed method (see, e.g., FIG. 2) and the associated discussion herein above can be defined by the computer program instructions stored in memory 430 and/or data storage device 420 and controlled by processor 410 executing the computer program instructions. For example, the computer program instructions can be implemented as computer executable code programmed by one skilled in the art to perform the illustrative operations defined by the disclosed method. Accordingly, by executing the computer program instructions, processor 410 executes an algorithm defined by the disclosed method. Computer 400 also includes one or more communication interfaces 450 for communicating with other devices via a network (e.g., a wireless communications network) or communications protocol (e.g., Bluetooth®). For example, such communication interfaces may be a receiver, transceiver or modem for exchanging wired or wireless communications in any number of well-known fashions. Computer 400 also includes one or more input/output devices 440 that enable user interaction with computer 400 (e.g., camera, display, keyboard, mouse, speakers, microphone, buttons, etc.).

Processor 410 may include both general and special purpose microprocessors, and may be the sole processor or one of multiple processors of computer 400. Processor 410 may comprise one or more central processing units (CPUs), for example. Processor 410, data storage device 420, and/or memory 430 may include, be supplemented by, or incorporated in, one or more application-specific integrated circuits (ASICs) and/or one or more field programmable gate arrays (FPGAs).

Data storage device 420 and memory 430 each comprise a tangible non-transitory computer readable storage medium. Data storage device 420, and memory 430, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 440 may include peripherals, such as a camera, printer, scanner, display screen, etc. For example, input/output devices 440 may include a display device such as a cathode ray tube (CRT), plasma or liquid crystal display (LCD) monitor for displaying information to the user, a keyboard, and a pointing device such as a mouse or a trackball by which the user can provide input to computer 400.

It should be noted that for clarity of explanation, the illustrative embodiments described herein may be presented as comprising individual functional blocks or combinations of functional blocks. The functions these blocks represent may be provided through the use of either dedicated or shared hardware, including, but not limited to, hardware capable of executing software. Illustrative embodiments may comprise digital signal processor ("DSP") hardware and/or software performing the operation described herein. Thus, for example, it will be appreciated by those skilled in the art that the block diagrams herein represent conceptual views of illustrative functions, operations and/or circuitry of the principles described in the various embodiments herein. Similarly, it will be appreciated that any flowcharts, flow diagrams, state transition diagrams, pseudo code, program code and the like represent various processes which may be substantially represented in computer readable medium and so executed by a computer, machine or processor, whether or not such computer, machine or processor is explicitly shown. One skilled in the art will recognize that an implementation of an actual computer or computer system may have other structures and may contain other components as well, and that a high level representation of some of the components of such a computer is for illustrative purposes.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIG. 2. Certain steps of the methods described herein, including one or more of the steps of FIG. 2, may be performed by a server or by another processor in a network-based cloud-computing system, and/or performed by a client computer in a network-based cloud computing system. The steps of the methods described herein may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIG. 2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

What is claimed is:

1. An ophthalmic illumination and microscopic viewing system, comprising:
    a laser light source configured to generate an alignment pattern formed from a patient-invisible wavelength;
    a processor configured to generate a composite image based on reflected light from an eye under examination resulting from the alignment pattern directed thereupon and based on information associated with the eye; and
    an optical system configured to receive the composite image generated by the processor and receive reflected light from the eye resulting from light directed thereupon, and transmit the received composite image and the received reflected light while superimposing the received composite image with the received reflected light to create a superimposed image.

2. The ophthalmic illumination and microscopic viewing system of claim 1, wherein the information associated with the eye comprises at least one of a treatment parameter, preoperative image, or treatment plan.

3. The ophthalmic illumination and microscopic viewing system of claim 1, wherein the information associated with the eye comprises eye measurement information.

4. The ophthalmic illumination and microscopic viewing system of claim 1, further comprising a treatment laser light source configured to generate therapeutic light.

5. The ophthalmic illumination and microscopic viewing system of claim 1, wherein the laser light source is configured to generate therapeutic light with a residual pump.

6. The ophthalmic illumination and microscopic viewing system of claim 5, wherein the alignment pattern and therapeutic light are coupled within a shared optical fiber, such that the alignment pattern and therapeutic light are co-aligned.

7. The ophthalmic illumination and microscopic viewing system of claim 5, wherein the therapeutic light is directed upon the eye in accordance with the alignment pattern.

8. The ophthalmic illumination and microscopic viewing system of claim 1, wherein the received composite image comprises an indication of the focus of the alignment pattern on the eye under examination.

9. The ophthalmic illumination and microscopic viewing system of claim 8, wherein the indication comprises a color change of the reflected light from the eye under examination resulting from the alignment pattern directed thereupon.

10. The ophthalmic illumination and microscopic viewing system of claim 1, further comprising a display system configured to display the superimposed image to a user.

11. The ophthalmic illumination and microscopic viewing system of claim 10, wherein:
the processor is configured to generate a thermal damage zone associated with the alignment pattern, and the processor generates the composite image to include the thermal damage zone; and
the display system is configured to display the thermal damage zone to the user.

12. The ophthalmic illumination and microscopic viewing system of claim 10, wherein the display system is a video system, and wherein the superimposed image is a frame within a video.

13. An ophthalmic illumination method, comprising:
generating an alignment pattern formed by a patient-invisible wavelength from a laser light source;
generating a composite image based on reflected light from an eye under examination resulting from the alignment pattern directed thereupon and based on information associated with the eye;
associating the generated composite image with reflected light from the eye resulting from light directed thereupon; and
transmitting the received composite image and the received reflected light while superimposing the received image with the received reflected light to create a superimposed image.

14. The ophthalmic illumination method of claim 13, wherein the information associated with the eye comprises at least one of a treatment parameter, preoperative image, or treatment plan.

15. The ophthalmic illumination method of claim 13, wherein the information associated with the eye comprises eye measurement information.

16. The ophthalmic illumination method of claim 13, further comprising generating a therapeutic light with a treatment laser light source.

17. The ophthalmic illumination method of claim 13, further comprising generating a therapeutic light with the laser light source with a residual pump.

18. The ophthalmic illumination method of claim 13, wherein generating a composite image further comprises computing a thermal damage zone associated with the alignment pattern.

19. The ophthalmic illumination method of claim 13, wherein generating a composite image further comprises indicating the focus of the alignment pattern on the eye under examination.

20. The ophthalmic illumination method of claim 13, further comprising displaying the superimposed image to a user via a heads up display system.

* * * * *